US008917319B2

(12) United States Patent
Igarashi et al.

(10) Patent No.: US 8,917,319 B2
(45) Date of Patent: Dec. 23, 2014

(54) IMAGE PROCESSING APPARATUS AND ENDOSCOPE SYSTEM

(71) Applicants: Olympus Medical Systems Corp., Tokyo (JP); Olympus Corporation, Tokyo (JP)

(72) Inventors: Makoto Igarashi, Hachioji (JP); Kenji Yamazaki, Sagamihara (JP); Tetsuo Nonami, Hino (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 20 days.

(21) Appl. No.: 13/782,038

(22) Filed: Mar. 1, 2013

(65) Prior Publication Data

US 2013/0176411 A1   Jul. 11, 2013

Related U.S. Application Data

(63) Continuation of application No. PCT/JP2012/059685, filed on Apr. 9, 2012.

(30) Foreign Application Priority Data

Sep. 20, 2011   (JP) .................................. 2011-204953

(51) Int. Cl.
*A61B 1/05* (2006.01)
(Continued)

(52) U.S. Cl.
CPC .............. *A61B 1/05* (2013.01); *G02B 23/2484* (2013.01); *A61B 1/00009* (2013.01);
(Continued)

(58) Field of Classification Search
CPC .... G01N 21/27; G02B 23/24; G02B 23/2484; G02B 26/008; H04N 9/04; A61B 1/05; A61B 1/00009; A61B 1/0638; A61B 1/0646; A61B 1/0669; A61B 1/0684; G06T 7/0012

USPC ........................................................... 348/65
See application file for complete search history.

(56) References Cited

U.S. PATENT DOCUMENTS 5,550,582 A    8/1996  Takasugi et al.
5,675,378 A   10/1997  Takasugi et al.
(Continued)

FOREIGN PATENT DOCUMENTS

EP   1 576 920 A1   9/2005
JP   02-271822    11/1990
(Continued)

OTHER PUBLICATIONS

International Search Report dated May 15, 2012 issued in PCT/JP2012/059685.

*Primary Examiner* — Andy Rao
*Assistant Examiner* — Nguyen Truong
(74) *Attorney, Agent, or Firm* — Scully, Scott, Murphy & Presser, P.C.

(57) ABSTRACT

An endoscope system includes a light source device, a CCD, a video processor, and an observation monitor, wherein the video processor includes: a band decomposition processing section that performs a decomposition processing for decomposing into a plurality of spatial frequency bands on a signal of an image picked up by the CCD, to generate a plurality of band images; an enhancement processing section that performs an enhancement processing on selected band images based on an enhancement amount set for a region where an observation target in a subject is distributed in a feature space formed with wavelength bands or spatial frequency bands of the band images selected among the plurality of band images as axes; and an image generation section that integrates the plurality of band images subjected to the color conversion processing, for each wavelength image, to generate an image.

14 Claims, 10 Drawing Sheets

(51) Int. Cl.
   *G02B 23/24*   (2006.01)
   *A61B 1/00*    (2006.01)
   *G02B 26/00*   (2006.01)
   *A61B 1/06*    (2006.01)
   *H04N 9/67*    (2006.01)
   *G06T 5/00*    (2006.01)

(52) U.S. Cl.
   CPC ............ *G02B 26/008* (2013.01); *A61B 1/0638* (2013.01); *A61B 1/0646* (2013.01); *A61B 1/0669* (2013.01); *H04N 9/67* (2013.01); *G06T 5/003* (2013.01); *A61B 1/0684* (2013.01); *G06T 2207/10016* (2013.01); *G06T 2207/10024* (2013.01); *G06T 2207/10068* (2013.01); *G06T 2207/10152* (2013.01); *G06T 2207/20192* (2013.01); *G06T 2207/30101* (2013.01)
   USPC .......................................................... 348/65

(56) References Cited

U.S. PATENT DOCUMENTS

2006/0241349 A1* 10/2006 Gono ........................... 600/160
2010/0195904 A1    8/2010 Tsuruoka

FOREIGN PATENT DOCUMENTS

| JP | 06-335451 | 12/1994 | | |
| JP | 09-035056 | 2/1997 | | |
| JP | 2000-148987 | 5/2000 | | |
| JP | 2004-202217 | 7/2004 | | |
| JP | 2008-023041 | * 2/2008 | ................ G06T 1/00 |
| JP | 2009-039561 | 2/2009 | | |
| JP | 2010-130636 | 6/2010 | | |
| WO | WO 2004/052187 A1 | 6/2004 | | |

* cited by examiner

IMAGE PROCESSING APPARATUS AND ENDOSCOPE SYSTEM

CROSS REFERENCE TO RELATED APPLICATION

This application is a continuation application of PCT/JP2012/059685 filed on Apr. 9, 2012 and claims benefit of Japanese Application No. 2011-204953 filed in Japan on Sep. 20, 2011, the entire contents of which are incorporated herein by this reference.

BACKGROUND OF THE INVENTION

1. Field of the Invention

The present invention relates to an image processing apparatus and an endoscope system, and more particularly to an image processing apparatus and an endoscope system which are configured to display a medical image obtained by picking up an image in a subject.

2. Description of the Related Art

Conventionally, various less-invasive examinations and surgeries using an endoscope have been performed in medical fields. A surgeon inserts an endoscope into a body cavity, to observe an image of a subject picked up by an image pickup apparatus provided at a distal end portion of an endoscope insertion portion, and is capable of performing treatment on a lesion part using a treatment instrument inserted in a treatment instrument channel, as needed. A surgery using an endoscope has an advantage of low physical burden on a patient, because there is no need for opening the abdomen.

An endoscope apparatus is configured by including an endoscope, an image processing apparatus connected to the endoscope, and an observation monitor. An image of a lesion part is picked up by an image pickup device provided at a distal end portion of an endoscope insertion portion and the picked-up image is displayed on the monitor. A surgeon can perform diagnosis or a necessary treatment while viewing the image displayed on the monitor.

Recently, also an endoscope apparatus which displays capillary vessels under the surface of a living tissue of a subject using narrow-band light has been developed. Such an endoscope apparatus irradiates a subject with illumination light of predetermined narrow bands to obtain images in the respective narrow bands from the light reflected from the subject, or irradiates the subject with illumination light which is white light to obtain predetermined narrow-band images by performing a spectral estimation processing on the image of the light reflected from the subject, thereby allowing the capillary vessels to be displayed.

In addition, as disclosed in Japanese Patent Application Laid-Open Publication No. 2000-148987, for example, also an image processing apparatus has been proposed, which extracts a desired frequency component from an RGB image and changes a signal level of the extracted frequency component such that a microstructure or a subtle change in a color tone of a surface of mucosa can be clearly observed.

Furthermore, as an endoscope apparatus, also an infrared endoscope apparatus has been proposed, which is capable of observing blood vessels inside a subject by injecting indocyanine green (ICG) having a characteristic of absorption peak in near-infrared light of wavelength near 805 nm into the blood of a patient as medicinal agent and irradiating the subject with infrared lights of wavelengths near 805 nm and near 930 nm from a light source apparatus in a time divisional manner, for example.

SUMMARY OF THE INVENTION

An image processing apparatus according to one aspect of the present invention includes: an image input section that receives a medical image picked up in a subject; a band decomposition processing section that performs a decomposition processing respectively on images in a plurality of wavelength bands in the medical image, to decompose the respective images into images in a plurality of spatial frequency bands and generate a plurality of band images; an enhancement amount setting section that sets an enhancement amount for a region where an observation target in the subject is distributed in a feature space, the feature space being a space formed so as to have, as axes, wavelength bands or spatial frequency bands of two or more band images selected among the plurality of band images generated by the band decomposition processing section according to the observation target in the subject, or being another space in which the space is projected; an enhancement processing section that performs an enhancement processing on the selected two or more band images, based on the enhancement amount set by the enhancement amount setting section; a color conversion processing section that performs a color conversion processing for adjusting color tone on the plurality of band images before the enhancement processing is performed thereon, or the plurality of band images including the selected two or more band images having been enhanced by the enhancement processing section; and an image generation section that integrates the plurality of band images subjected to the color conversion processing by the color conversion processing section, for each wavelength image, to generate an image.

An endoscope system according to one aspect of the present invention includes: an illuminating section that irradiates light having a plurality of wavelength bands to a subject; an image pickup section that picks up an image of returned light of the light irradiated to the subject by the illuminating section; a band decomposition processing section that performs a decomposition processing for decomposing into a plurality of spatial frequency bands on a signal of the image picked up by the image pickup section and generates a plurality of band images; an enhancement amount setting section that sets an enhancement amount for a region where a blood vessel which exists in a depth direction of a living mucosa in the subject is distributed in a feature space, the feature space being a space formed so as to have, as axes, wavelength bands or spatial frequency bands of two or more band images selected among the plurality of band images generated by the band decomposition processing section, or being another space in which the space is projected; an enhancement processing section that performs an enhancement processing on the selected two or more band images, based on the enhancement amount set by the enhancement amount setting section; a color conversion processing section that performs a color conversion processing for adjusting color tone on the plurality of band images before the enhancement processing is performed thereon, or the plurality of band images including the selected two or more band images having been enhanced by the enhancement processing section; an image generation section that integrates the plurality of band images subjected to the color conversion processing by the color conversion processing section, for each wavelength image, to generate an image; a display signal output section that outputs an integrated image outputted from the image generation section as a display signal; and a display section that performs display based on the display signal outputted from the display signal output section.

DETAILED DESCRIPTION OF THE PREFERRED EMBODIMENT(S)

Hereinafter, an embodiment of the present invention is described with reference to drawings.
(Configuration)

Figure 1:
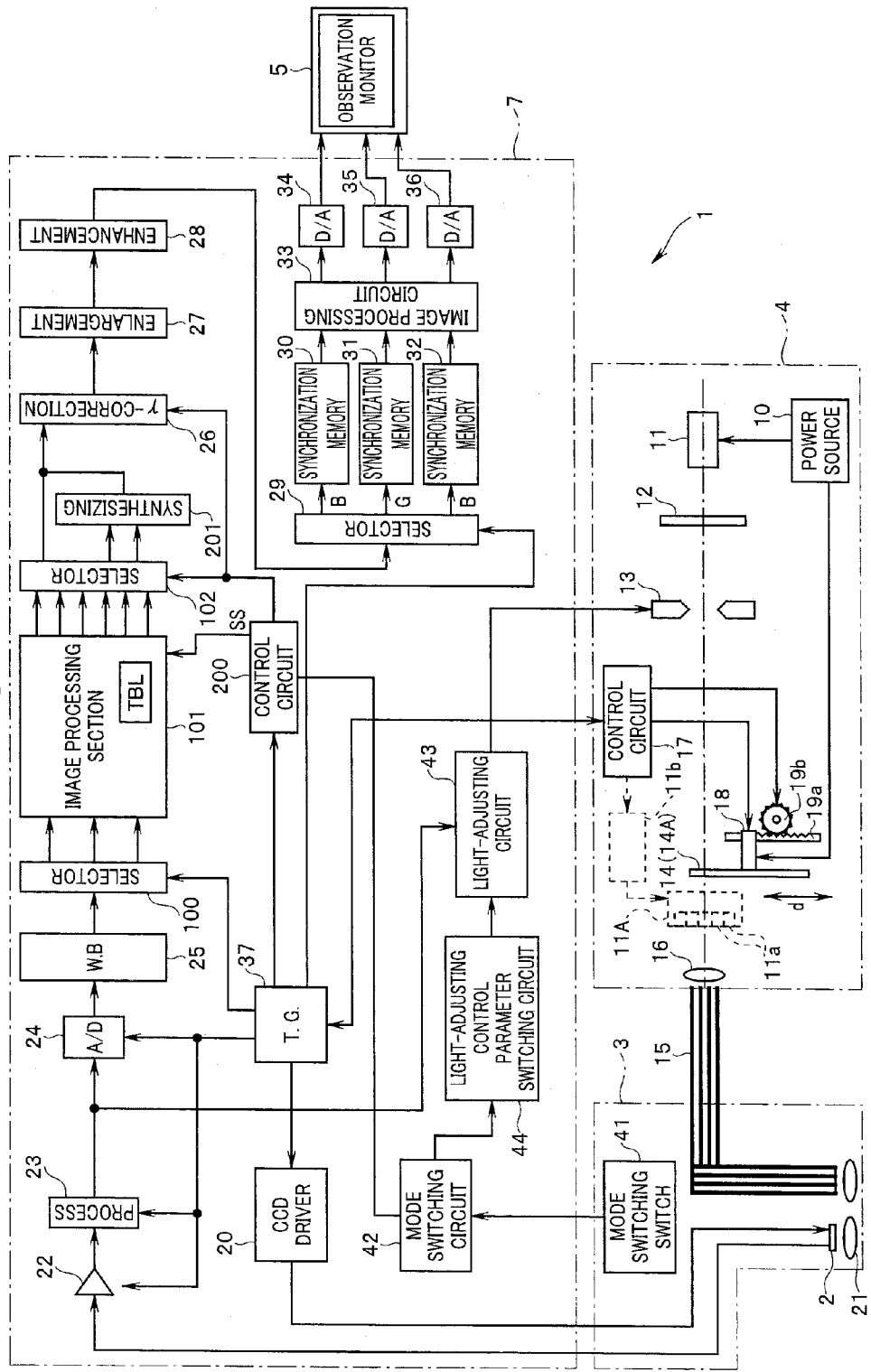
FIG. 1 is a configuration diagram illustrating a configuration of an endoscope system according to an embodiment of the present invention.

FIG. 1 is a configuration diagram illustrating a configuration of an endoscope system according to a present embodiment.

As shown in FIG. 1, an endoscope system 1 according to the present embodiment includes an electronic endoscope 3 including a CCD 2 which is an image pickup device, as living body image information acquiring means which is inserted into a body cavity to pick up an image of a tissue in the body cavity, a light source device 4 which supplies illumination light to the electronic endoscope 3, and a video processor 7 which performs a signal processing on an image pickup signal from the CCD 2 of the electronic endoscope 3 and displays an endoscopic image on an observation monitor 5. The endoscope system 1 has two modes, that is, a normal light observation mode and a narrow-band light observation mode. Note that, since the normal light observation mode in the endoscope system 1 is the same as the conventional normal light observation mode, the configuration of the normal light observation mode is briefly described in the description below, and the narrow-band light observation mode is mainly described.

The CCD 2 configures an image pickup section or image pickup means which picks up an image of return light of the light irradiated to a subject by illumination means.

The light source device 4 includes: a xenon lamp 11 as an illuminating section which emits illumination light (white light); a heat ray cut-off filter 12 which cuts off heat rays of white light; a diaphragm device 13 which controls the light amount of white light having passed through the heat ray cut-off filter 12; a rotary filter 14 as band-limiting means which changes the illumination light to a frame-sequential light; a condensing lens 16 which condenses the frame-sequential light, which has passed through the rotary filter 14, on a light incident surface of a light guide 15 disposed in the electronic endoscope 3; and a control circuit 17 which controls rotation of the rotary filter 14. The xenon lamp 11, the rotary filter 14, and the light guide 15 configure an irradiation section or irradiation means which illuminates illumination light to a subject.

Note that as shown in the dotted lines in FIG. 1, the light source device 4 may be configured so as to include a light-emitting section 11A having a light-emitting diode group 11a composed of a plurality of light-emitting diodes (LEDs) which emit desired wavelengths, for example, the respective RGB wavelengths corresponding to a first filter group, and the respective wavelengths near 540 nm, 600 nm, and 630 nm corresponding to a second filter group.

For example, in FIG. 1, the light source device 4 is provided with the light-emitting section 11A shown by the dotted lines, instead of the xenon lamp 11, the heat ray cut-off filter 12, the diaphragm device 13, the rotary filter 14, and the like. Furthermore, the light source device 4 is provided with a driving circuit 11b for driving the respective light-emitting diodes of the light-emitting section 11A at predetermined timings according to the respective modes. The light-emitting section 11A having the plurality of LEDs 11a receives power supply from a power source 10, and is controlled and driven by the driving circuit 11b under the control signal from the control circuit 17.

Furthermore, the light-emitting section 11A may use a laser diode (LD) which emits light of a plurality of predetermined narrow bands. Accordingly, the light source device 4 configures the illuminating section which irradiates the subject with the light having a plurality of wavelength bands.

Figure 2:
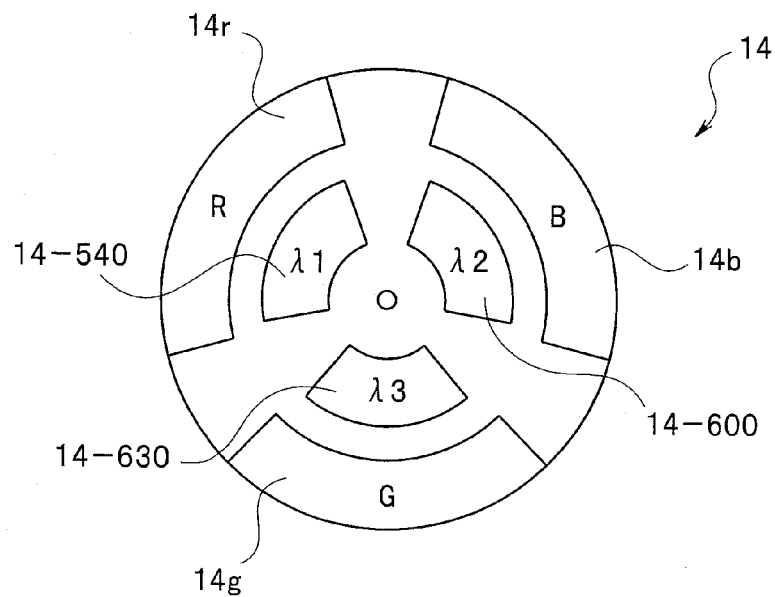
FIG. 2 illustrates a configuration of a rotary filter 14 according the embodiment of the present invention.

FIG. 2 illustrates the configuration of the rotary filter 14. As shown in FIG. 2, the rotary filter 14 as a wavelength band-limiting section or wavelength band-limiting means is configured to have a disk shape with the center being a rotational axis, and include two filter groups. On the outer circumferential side of the rotary filter 14, an R (red) filter section 14r, a G (green) filter section 14g, and a B (blue) filter section 14b, which compose a filter set for outputting a frame-sequential light having spectral characteristics for normal observation, are disposed as a first filter group along a circumferential direction.

On the inner circumferential side of the rotary filter 14, three filters 14-540, 14-600, and 14-630 which transmit lights of three predetermined narrow-band wavelengths are disposed along the circumferential direction, as a second filter group.

The filter 14-540 is configured to transmit light of wavelength near 540 nm as narrow-band light. The filter 14-600 is configured to transmit light of wavelength near 600 nm as narrow-band light. The filter 14-630 is configured to transmit light of wavelength near 630 nm as narrow-band light.

Note that the filter 14-540 may transmit the light of wavelength near 460 nm or the light of wavelength near 415 nm as narrow-band light.

In addition, the number of filters is not limited to three, but may be two, or four or more. When two filters are provided, it is possible to combine two filters which respectively transmit lights of wavelengths 540 nm and 600 nm, two filters which respectively transmit lights of wavelengths 540 nm and 630 nm, or two filters which respectively transmit lights of wavelengths 460 nm and 600 nm, for example. When four filters are provided, it is possible to combine four filters which respectively transmit wavelengths 460 nm, 540 nm, 600 nm, and 630 nm, for example.

In the present embodiment, lights of wavelengths near 600 nm and 630 nm which are red bands in the visible range and at which hemoglobin optical absorption characteristics sharply decrease are used as narrow-band lights. In the present embodiment, the term "near" means that, in the case of near the wavelength of 600 nm, the light is a narrow-band light having a center wavelength of 600 nm and having a distribution in a range of width of, for example, 20 nm centering around the wavelength of 600 nm (i.e., a wavelength of 590 nm to a wavelength of 610 nm around the wavelength of 600 nm). The same is true for other wavelengths, that is, the wavelength 630 nm, and the wavelength 540 nm, to be described later.

The rotary filter 14 is arranged on the optical path from the xenon lamp 11 as the emitting section of the illumination light to the image pickup surface of the CCD 2, to limit the wavelength bands so as to narrow at least two of a plurality of wavelength bands of the illumination light.

In addition, the control circuit 17 controls the motor 18 for rotating the rotary filter 14, to control the rotation of the rotary filter 14.

The motor 18 is connected with a rack 19a, a pinion 19b is connected with a motor, not shown, and the rack 19a is attached so as to screw with the pinion 19b. The control circuit 17 controls the rotation of the motor connected to the pinion 19b, thereby capable of moving the rotary filter 14 in the direction shown by the arrow d. Therefore, the control circuit 17 selects the first filter group or the second filter group in accordance with the mode switching operation by the user, which will be described later.

Note that power is supplied from the power source section 10 to the xenon lamp 11, the diaphragm device 13, the rotary filter motor 18, and the motor (not shown) connected to the pinion 19b.

The video processor 7 as the image processing apparatus is configured by including: a CCD driving circuit 20 as a CCD driver; an amplifier 22; a process circuit 23; an A/D converter 24; a white balance circuit (hereinafter abbreviated as W. B) 25; a selector 100; an image processing section 101; a selector 102; a γ-correction circuit 26; an enlargement circuit 27; an enhancement circuit 28; a selector 29; synchronization memories 30, 31 and 32; an image processing circuit 33; D/A converters 34, 35 and 36; a timing generator (hereinafter abbreviated as T. G) 37; a control circuit 200; and a synthesizing circuit 201 as display image generation means.

The CCD driving circuit 20 drives the CCD 2 provided in the electronic endoscope 3 and outputs a frame-sequential image pickup signal synchronized with the rotation of the rotary filter 14. In addition, the amplifier 22 amplifies the frame-sequential image pickup signal which has been obtained by picking up an image of a tissue inside the body cavity with the CCD 2 through an objective optical system 21 provided at the distal end of the electronic endoscope 3.

The process circuit 23 performs correlated double sampling, noise removal and the like on the frame-sequential image pickup signal having passed through the amplifier 22. The A/D converter 24 converts the frame-sequential image pickup signal, which has passed through the process circuit 23, into a digital frame-sequential image signal.

The W. B 25 performs gain control and a white balance processing on the frame-sequential image signal, which has been digitized by the A/D converter 24, such that an R signal of the image signal and a B signal of the image signal have an equal brightness with a G signal of the image signal used as a reference, for example.

The selector 100 outputs the frame-sequential image signal from the W. B 25 dividedly to respective parts of the image processing section 101.

The amplifier 22, the process circuit 23, and the A/D converter 24, the W. B 25 and the selector 100, which receive the image pickup signal from the electronic endoscope 3 and perform a processing thereon, configure an image input section into which a medical image picked up in the subject is inputted.

The image processing section 101 is an image signal processing section or image signal processing means which converts RGB image signals for normal light observation or two image signals for narrow-band light observation, which are sent from the selector 100, into an image signal for display. The image processing section 101 outputs image signals in the normal light observation mode and the narrow-band light observation mode to the selector 102 in response to a selection signal SS from the control circuit 200 based on a mode signal.

The selector 102 sequentially outputs a frame-sequential image signal of the image signal for normal light observation and the image signal for narrow-band light observation from the image processing section 101 to the γ-correction circuit 26 and the synthesizing circuit 201.

The γ-correction circuit 26 performs a γ-correction processing on the frame-sequential image signal from the selector 102 or the synthesizing circuit 201. The enlargement circuit 27 performs an enlargement processing on the frame-sequential image signal subjected to the γ-correction processing in the γ-correction circuit 26. The enhancement circuit 28 performs a contour enhancement processing on the frame-sequential image signal subjected to the enlargement processing in the enlargement circuit 27. The selector 29 and the synchronization memories 30, 31 and 32 are used for synchronizing the frame-sequential image signal from the enhancement circuit 28.

The image processing circuit 33 reads out the respective frame-sequential image signals stored in the synchronization memories 30, 31, and 32 and performs a moving image color drift correction processing on the read-out signals. The D/A converters 34, 35, and 36 convert the image signal from the image processing circuit 33 into RGB analog video signals and output the RGB analog video signals to the observation monitor 5. The T. G 37 receives input of a synchronization signal, which has been synchronized with the rotation of the rotary filter 14, from the control circuit 17 of the light source device 4 and outputs various timing signals to the respective circuits in the video processor 7. The circuits from the selector 102 to the D/A converters 34, 35, and 36 configure the display signal output section which outputs a band image, to be described later, outputted from the image processing section 101 as a display signal. Then, the observation monitor 5 configures a display section which displays an image based on the display signal outputted from the display signal output section.

In addition, the electronic endoscope 3 is provided with a mode switching switch 41 for switching between the normal light observation mode and the narrow-band light observation mode, and the output of the mode switching switch 41 is outputted to a mode switching circuit 42 in the video processor 7. The mode switching circuit 42 in the video processor 7 is configured to output a control signal to a light-adjusting control parameter switching circuit 44 and the control circuit 200. The light-adjusting circuit 43 controls the diaphragm device 13 of the light source device 4 and performs proper brightness control based on light-adjusting control parameters from the light-adjusting control parameter switching circuit 44 and the image pickup signal having passed through the process circuit 23.

The respective circuits in the video processor 7 perform a predetermined processing according to the specified mode. Processing in accordance with each of the normal light observation mode and the narrow-band light observation mode is performed, and a normal light observation image or a narrow-band light observation image is displayed on the observation monitor 5.

(Flow of Whole Processing)

Next brief description will be made on a whole flow of the narrow-band light observation according to the present embodiment.

Figure 3:
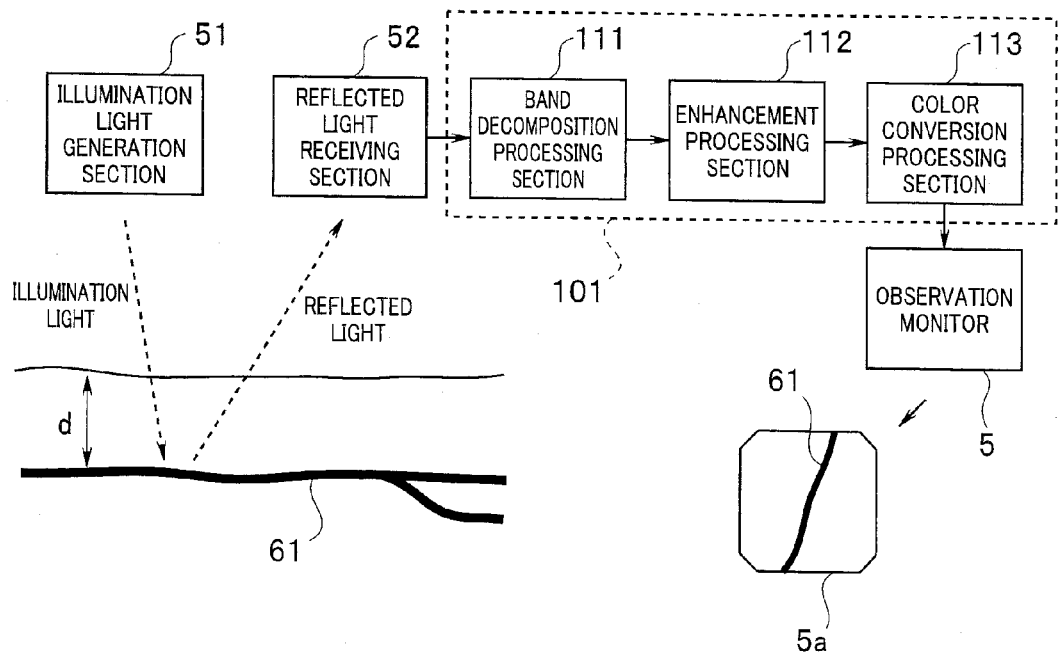
FIG. 3 illustrates a flow of whole processing in a narrow-band observation according to the embodiment of the present invention.

FIG. 3 illustrates the flow of the whole processing in the narrow-band light observation according to the present embodiment.

The surgeon inserts the insertion portion of the endoscope into the body cavity and locates the distal end portion of the insertion portion of the endoscope in the vicinity of a lesion part under the normal observation mode. When identifying the lesion part to be treated, the surgeon operates the mode switching switch 41 to switch the endoscope system 1 to the narrow-band observation mode, in order to observe a relatively thick blood vessel 61 having a diameter of, for example, 1 to 2 mm, and running through a position at a depth d under the mucosa. In this case, the blood vessel 61 is an observation target and an object existing in the depth direction of the living mucosa.

Under the narrow-band observation mode, the control circuit 17 in the endoscope system 1 controls the motor connected to the pinion 19b to move the position of the rotary filter 14, such that the light passed through the second filter group is emitted from the light source device 4. Furthermore, the control circuit 200 also controls various circuits in the video processor 7 so as to perform an image processing for observation with narrow-band wavelengths.

As shown in FIG. 3, in the narrow-band mode, the illumination light of narrow-band wavelength from an illumination light generation section 51 is emitted from the distal end portion of the insertion portion of the endoscope 3, to be transmitted through the stratum mucosum and irradiated to the blood vessel 61 running through a submucosal layer and a muscularis propria. The illumination light generation section 51 is configured by including the light source device 4, the rotary filter 14, the light guide 15 and the like, and emits illumination light from the distal end of the insertion portion of the endoscope. The rotation of the rotary filter 14 causes the narrow-band light of wavelength near 540 nm, the narrow-band light of wavelength near 600 nm, and the narrow-band light of wavelength near 630 nm to be alternately emitted from the light source device 4 to irradiate the subject.

Reflected lights of the narrow-band light of wavelength near 540 nm, the narrow-band light of wavelength near 600 nm, and the narrow-band light of wavelength near 630 nm are respectively received by a reflected light receiving section 52 as the CCD 2. The CCD 2 outputs image pickup signals of the respective reflected lights and the outputted image pickup signals are supplied to the selector 100 via the amplifier 22 and the like. The selector 100 maintains the images of the respective wavelengths (hereinafter, referred to as wavelength images) and supplies the images to the image processing section 101 according to predetermined timings from the T. G 37. Here, the three wavelength images (image of the wavelength near 540 nm (hereinafter referred to as λ1 image), image of the wavelength near 600 nm (hereinafter referred to as λ2 image), and image of the wavelength near 630 nm (hereinafter referred to as λ3 image)) are supplied to the image processing section 101.

The image signal processed in the image processing section 101 is outputted to the selector 102, and thereafter subjected to processings such as correction. As a result, an image of the subject is displayed on the observation monitor 5.

(Configuration of Image Processing Section)

The image processing section 101 includes a band decomposition processing section 111, an enhancement processing section 112 and a color conversion processing section 113, as shown in FIG. 3. The image processing section 101 receives three wavelength images, and performs a band decomposition processing, an enhancement processing and a color conversion processing on the wavelength images, and thereafter outputs the respective wavelength images.

(1) Band Decomposition Processing (Spatial Frequency Dividing Processing)

Figure 4:
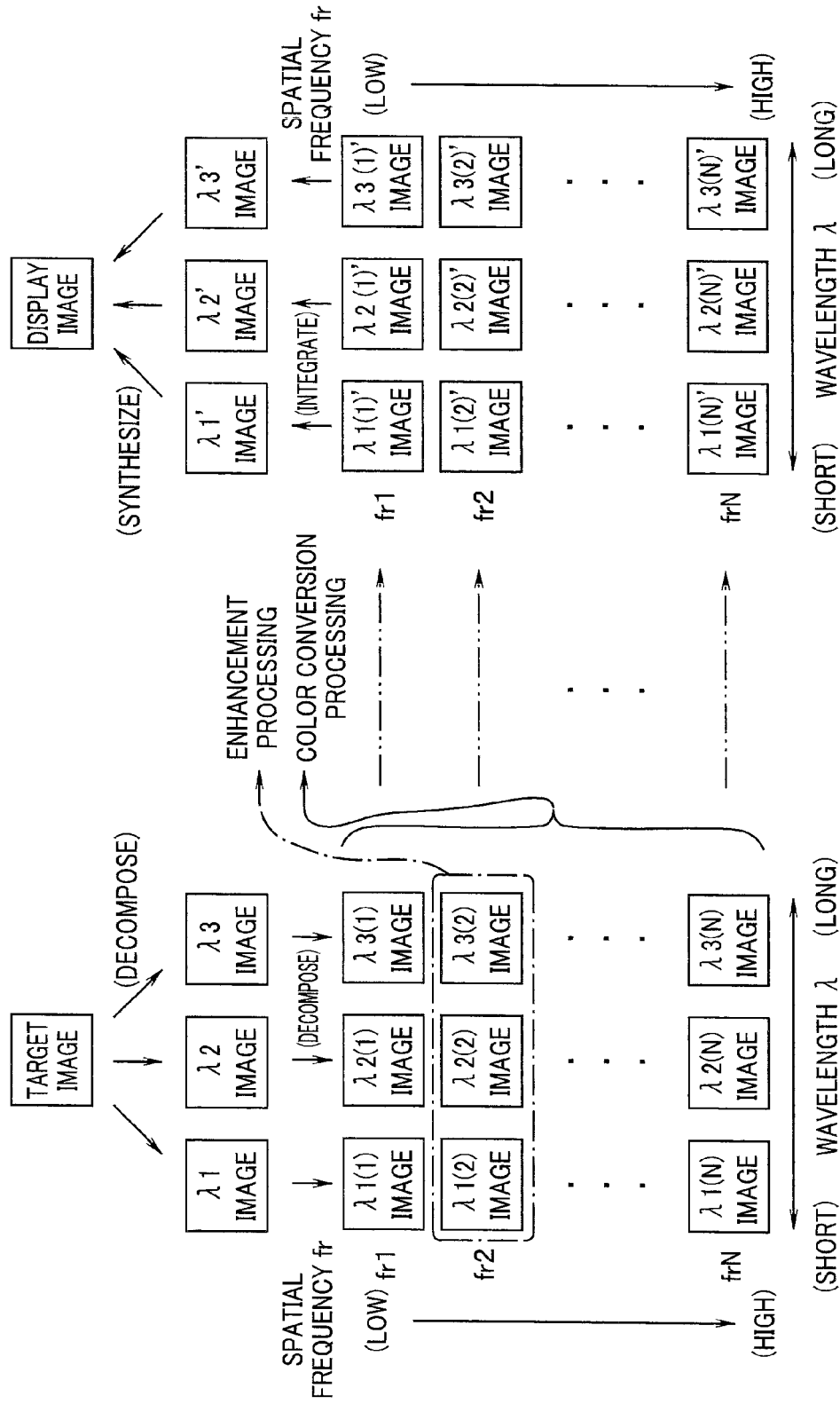
FIG. 4 illustrates a processing according to the embodiment of the present invention, in which images in a plurality of frequency bands are generated from a plurality of wavelength images and an enhancement processing and the like is performed on the generated plurality of images in the plurality of frequency bands.

The band decomposition processing section 111 performs a spatial frequency dividing processing on the respective wavelength images by the spatial frequency dividing processing. FIG. 4 illustrates a processing in which images in a plurality of frequency bands are generated from a plurality of wavelength images and an enhancement processing and the like are performed on the generated images in the plurality of frequency bands.

As shown in FIG. 4, the band decomposition processing section 111 divides the λ1 image into images (hereinafter referred to as band images) of N (N is a positive integer equal to or larger than 1) spatial frequency bands by spatial frequency analysis, i.e., spatial frequency dividing processing. Similarly, the band decomposition processing section 111 respectively divides the λ2 image and the λ3 image into N band images. That is, the band decomposition processing section 111 generates one, or two or more band images, i.e., N band images with respect to respective m (m is positive integer equal to or larger than 2) wavelength images. In the present embodiment, m is 3, and 3×N band images are generated from the three narrow-band images, that is, the λ1, λ2, and λ3 images.

Note that, when N is 1, three band images are generated. In this case, the wavelength images may be used as-is as band images and the next enhancement processing may be performed thereon.

Therefore, the band decomposition processing section 111 configures band decomposition processing means or spatial frequency dividing processing means which generates a plurality of band images by performing a processing for decomposing the medical image into images in a plurality of wavelength bands, or performing a decomposition processing on each of the wavelength bands of the medical image into a plurality of spatial frequency bands.

The N spatial frequency bands are spatial frequencies fr1, fr2, frN in the present embodiment. Hereinafter, it is supposed that the band image of the spatial frequency frk (k is any one of 1 to N) of the km image is referred to as λm (k) image such that the band image with the spatial frequency fr1 of the λ1 image is referred to as λ1 (1) image, and the band image with the spatial frequency fr2 of the λ1 image is referred to as λ1(2) image.

The respective band images are generated by performing a spatial frequency filtering processing on the respective wavelength images using masks corresponding to the respective spatial frequencies frk, for example.

(2) Enhancement Processing

The enhancement processing section 112 performs the enhancement processing on one, or two or more band images selected from the plurality of band images generated in the band decomposition processing section 111. FIG. 4 illustrates that the band images λ1 (2), λ2 (2), and λ3 (2) surrounded by a frame of the one-dot chain line are selected and the enhancement processing is performed thereon.

The enhancement processing is a processing for enhancing the respective selected band images, which is preformed by multiplying a predetermined enhancement coefficient to the pixel values of the respective pixels of the respective band images. In this processing, the respective band images are enhanced using a table TBL (see FIG. 1) which stores enhancement coefficients with respect to the respective pixel values, based on table data in the table.

Figure 5:
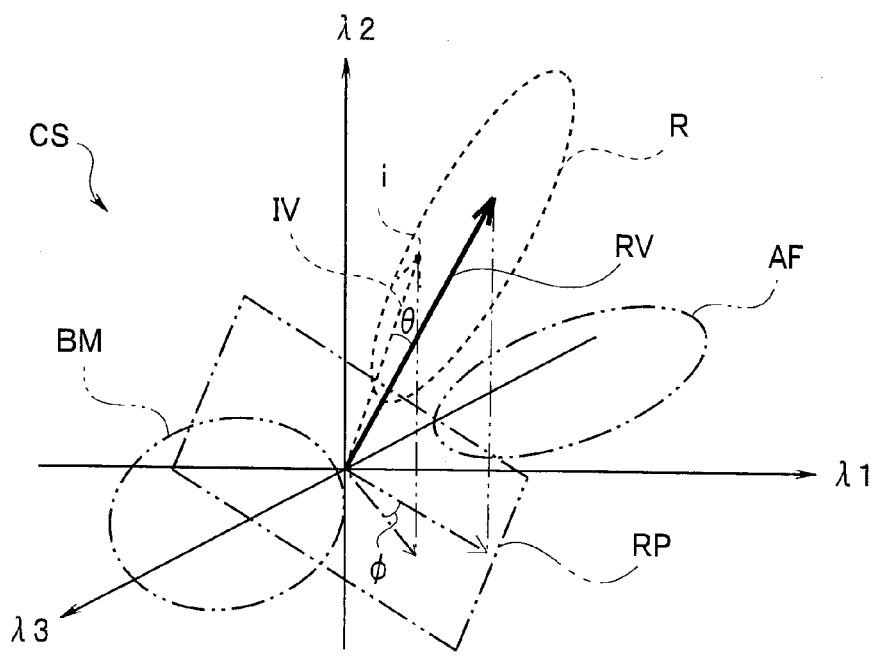
FIG. 5 relates to the embodiment of the present invention and illustrates a feature space including a region on which the enhancement processing is performed.

FIG. 5 illustrates a feature space including a region on which the enhancement processing is performed.

Figure 11:
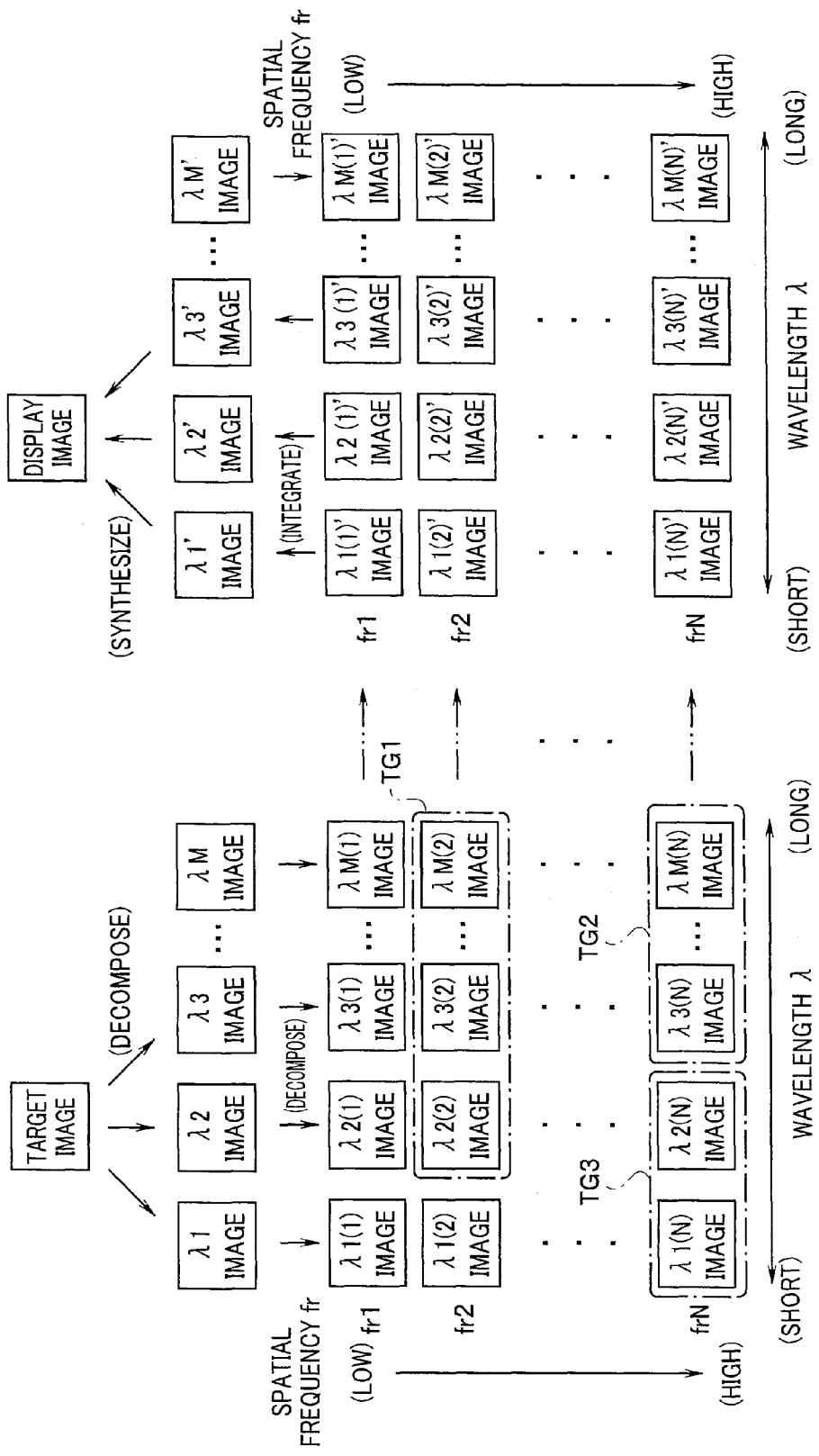
FIG. 11 relates to the embodiment of the present invention and illustrates a processing in which images in a plurality of frequency bands are generated from a plurality of wavelength images and an enhancement processing and the like are performed on targets at a plurality of desired depths in the generated images in the plurality of frequency bands.

Note that description is made here on an example of the feature space CS formed by three wavelength axes of narrow-band lights, but the feature space may be a feature space framed by two wavelength axes of narrow-band lights selected from the plurality of narrow-band lights, or may be a feature space formed by four or more wavelength axes as shown in FIG. 11 to be described later. Furthermore, the feature space may be a feature space formed by multiple axes including a spatial frequency axis in addition to the wavelength axes of the narrow-band lights, or a feature space formed only by a plurality of spatial frequency axes.

In FIG. 5, the region R shown by the dotted line shows a pixel distribution of a blood vessel image at a desired depth in the feature space CS formed by three axes of the respective wavelengths λ1, λ2 and λ3. The blood vessel at the desired depth is a target to be observed, and is an object which exists in the depth direction of the living mucosa. That is, the image having pixel values existing in the region R in the feature space CS in FIG. 5 corresponds to the image of the blood vessel at the desired depth d. In addition, the enhancement coefficients with respect to the pixels existing in the region R, which are used for displaying the blood vessel in an enhanced manner, differ from each other according to the positions in the feature space CS.

In FIG. 5, the point i represents a point corresponding to a certain pixel value data in the region R, and a vector of the point i from the origin is shown as a point vector IV. The respective enhancement coefficients α are set in advance so as to differ according to the angle θ formed by the point vector IV with respect to a reference vector RV corresponding to the region R in the feature space CS, for example. In order to enhance the pixels in the region R, the respective enhancement coefficients α are set so that the larger the angle θ formed by the point vector IV with respect to the reference vector RV becomes, the smaller the enhancement coefficient becomes. That is, the reference vector RV is set with respect to a predetermined distribution data in the feature space CS, and the angle displacement amount is calculated with respect to the observation target in the feature space CS, thereby setting an enhancement amount.

The enhancement coefficients are set by the control circuit 200. The control circuit 200 sets the enhancement coefficients by storing the enhancement coefficients data as the enhancement amount in the table TBL in the image processing section 101 as table data, based on the input into an operation panel, keyboard, or the like, not shown, of the processor 7. The enhancement coefficient data is determined by a user.

Accordingly, the control circuit 200 and the operation panel configure an enhancement amount setting section which set the enhancement amount with respect to the region where the observation target at the desired depth is distributed. Then, the enhancement processing is performed on the selected two or more band images based on the enhancement amount set by the enhancement amount setting section.

Note that polar coordinate transformation may be performed on the coordinates of a point in the feature space CS formed by three axes of the respective wavelengths λ1, λ2, and λ3, and the enhancement coefficient α may be defined by polar coordinates. In that case, the polar coordinates are defined by a zenith angle θ and an azimuth angle φ in FIG. 5.

Figure 6:
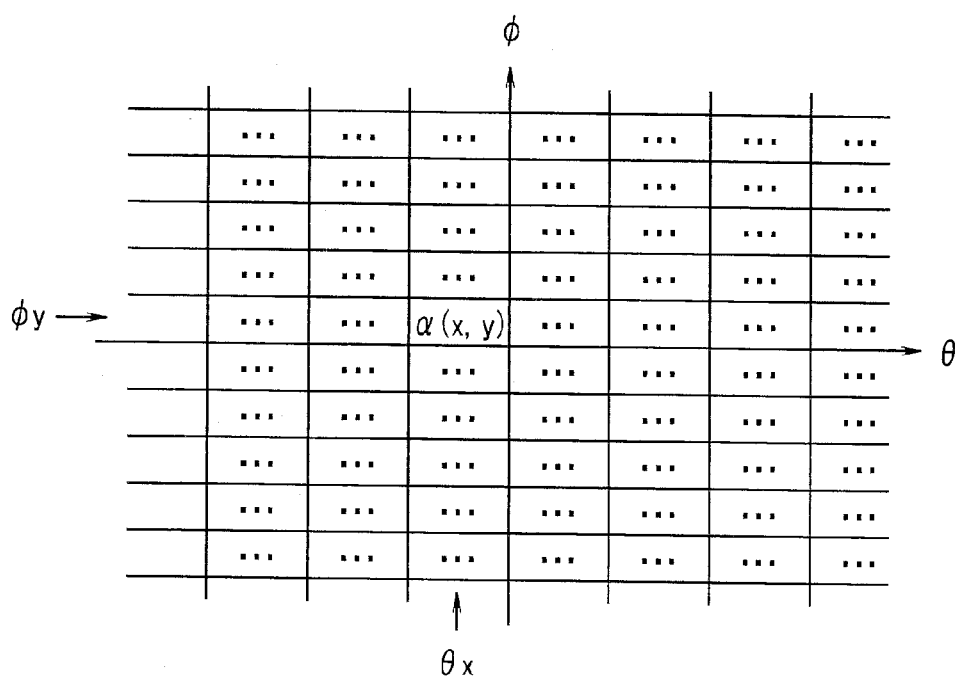
FIG. 6 relates to the embodiment of the present invention and illustrates an example of an enhancement table set using a polar coordinate.

FIG. 6 illustrates an example of an enhancement table set using the polar coordinates. The enhancement coefficient table TBL is a table based on the polar coordinates for the positions of the pixel values with respect to the reference vector RV. The table TBL stores data of the enhancement amount determined by the zenith angle θ and the azimuth angle φ, as the polar coordinates. In FIG. 6, α (x, y) represents the enhancement coefficient corresponding to the coordinates defined by the azimuth angle φx and the zenith angle θy.

In the case shown in FIG. 4, the band images λ1 (2), λ2 (2), and λ3 (2) are selected and the enhancement processing is performed thereon.

The respective pixels in the respective image frames of the band images λ1 (2), λ2 (2), and λ3 (2) are mapped at any positions in the feature space CS in FIG. 5. For example, when the angle formed by the vector IV of the point i which corresponds to a certain pixel mapped in the feature space CS and the reference vector RV is A, the enhancement coefficient α is set such that the angle range to be enhanced with respect to the pixels of the respective band images is a range defined by $0 \leq \theta \leq \pm(\pi/2)$ and including, in particular, the pixels in the region R, and the pixels are not enhanced in the region other than the above-described range or the region defined by $\theta \geq \pm (\pi/2)$. That is, in FIG. 5, it is supposed that the plane perpendicular to the reference vector RV is RP, the enhancement processing is performed on the pixels positioned on the side of the reference vector RV with respect to the plane RP in the feature space, and the enhancement processing is not performed on the pixels not positioned on the side of the reference vector RV with respect to the plane RP in the feature space.

The enhancement coefficient α with respect to each pixel, which is used for the enhancement processing, is determined using the following equation, for example. The reference sign α represents the enhancement coefficient with respect to the point i in the feature space.

$$\alpha i = (((\pi/2) - \theta)^2 \qquad \text{Equation (1)}$$

In the equation, r is an arbitrary real number.

The enhancement coefficient α with respect to each of the points in the region R in the feature space CS may be obtained for each point by the calculation using Equation (1) when the enhancement processing is performed, and may be multiplied to the pixel value of the pixel corresponding to the point i, for example. However, in the present embodiment, as described above, in order to perform the enhancement processing at a high speed, the enhancement coefficient α is calculated in advance for each point in the feature space CS using Equation (1), and stored in the memory in the image processing section 101 as an enhancement coefficient table TBL, and the enhancement processing section 112 in the image processing section 101 multiplies the enhancement coefficient to the pixel values using the data in the enhancement coefficient table TBL when performing the enhancement processing.

Here, description is made on the setting of the enhancement coefficient table TBL.

Figure 7:
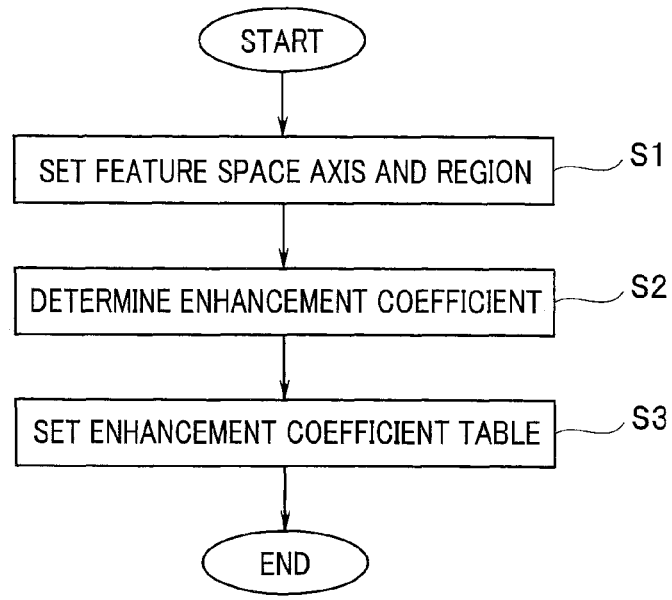
FIG. 7 is a flowchart showing a processing for setting an enhancement coefficient table according to the embodiment of the present invention.

FIG. 7 is a flowchart of a processing for setting the enhancement coefficient table. A user sets, i.e., selects two or more axes and a region in the feature space CS according to the depth of the tissue surface (S1). In the example shown in FIG. 5, the axes of the wavelength λ1 which is wavelength 540 nm of the λ1 image, the wavelength λ2 which is wavelength 600 nm of the λ2 image, and the wavelength λ3 which is wavelength 630 nm of the λ3 image, and the region R in the feature space CS formed by the three axes are set. The setting of the axes in the feature space CS differs according to an observation target at a desired depth d under the living tissue surface.

Therefore, the processing in S1 configures feature space forming means which finials a feature space with respect to the wavelength band decomposed into a plurality of wavelength bands by the band decomposition processing section 111 or a plurality of spatial frequency bands by selecting an arbitrary band from the plurality of bands in accordance with the observation target in the subject.

The user determines enhancement coefficients with respect to the set region (S2). In the example shown in FIG. 5, the enhancement amount at each point in the region R is calculated and determined based on above-described Equation (1).

The user stores and sets the respective enhancement coefficients calculated and determined in the step S2 in the enhancement coefficient table TBL (S3).

In the above-described processing steps, when the user specifies a feature space and a region on which the enhancement processing is performed, the user executes the processing steps in S1 to S3 by using a personal computer and the like, thereby capable of determining the enhancement coefficients and set the enhancement coefficients in the enhancement coefficient table TBL.

As described above, the enhancement amount for each of the pixels is set in the enhancement coefficient table TBL.

In the case shown in FIG. 4, the enhancement processing is performed on the pixels in the region R in the feature space CS in the band images λ1 (2), λ2 (2) and λ3 (2) selected for enhancing a blood vessel or the like at a desired depth by using the set enhancement coefficient table TBL.

The three wavelength images (λ1 image, λ2 image, and λ3 image) include images of the artifact AF and the background mucosa BM. However, as described above, since only the image in the desired region is enhanced, the images of the artifact AF and the background mucosa BM are not enhanced. FIG. 5 shows the region of the artifact AF. For example, the artifact AF is a region of the tissue injury site (black region) created when the tissue is incised and stripped off.

That is, the enhancement coefficient table TBL corresponding to the region R is created such that only the region R is enhanced excluding the regions of the artifact AF, the background mucosa Blvl and the like, thereby allowing the band images λ1 (2), λ2 (2) and λ3 (2) to be enhanced.

Furthermore, in the example shown in FIG. 5, the enhancement coefficient table TBL is created so as to enhance only the region R. However, a plurality of enhancement coefficient tables may be created so as to enhance a plurality of regions in the feature space CS.

Figure 8:
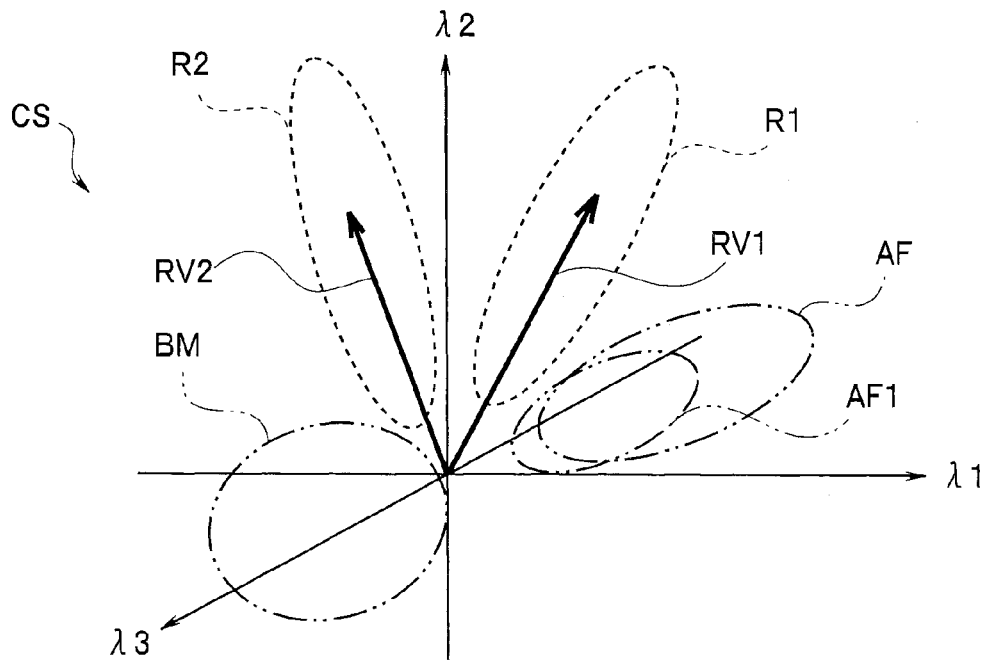
FIG. 8 relates to the embodiment of the present invention and illustrates a case where a plurality of regions are enhanced.

FIG. 8 illustrates a case where a plurality of regions are enhanced. In FIG. 8, two regions R1, R2 are set, and enhancement coefficients are set for the two regions R1, R2. In FIG. 8, reference vectors RV1, RV2 are set for the two regions R1, R2, respectively. The enhancement coefficients are determined in the respective regions, and set in advance in an enhancement coefficient tables TBL1 and TBL2.

As shown in FIG. 8, only the regions R1 and R2 are enhanced, and the enhancement coefficients become smaller with respect to the values of the pixels which are located at positions where the angles with respect to the two reference vectors RV 1, RV2 become larger. As a result, enhancement of the region AF of the image of the artifact and the region BM of the image of the background mucosa becomes weak.

In addition, a plurality of artifacts may be set, to set the enhancement coefficient for the region R. As shown in FIG. 8, two artifacts AF, AF1 are set, and the enhancement coefficient can be set so as not to enhance such artifacts. In FIG. 8, the artifact AF 1 is a region of a pigment such as indigo carmine, for example.

The feature space CS and the regions R, R1, and R2 shown in FIG. 5 and FIG. 8 are respectively set for different observation targets in accordance with the blood vessel and the like at desired depths under the mucosa. Therefore, the user creates, in advance, the enhancement coefficient tables corresponding to the feature space and the regions according to the blood vessel and the like at the desired depths under the mucosa, which the user wishes to enhance, such that a blood vessel and the like at an arbitrary depth under the mucosa can be enhanced. According to such a configuration, if the user specifies the blood vessel and the like at the depth which the user wishes to enhance under the mucosa, a corresponding enhancement table is selected and the enhancement processing for enhancing the blood vessel and the like at the desired depth can be performed.

In addition, the enhancement amount is set such that blood vessels in the living body, the background mucosa and other objects are not enhanced in the feature space CS.

As described above, the enhancement processing section 112 configures enhancement processing means which performs the enhancement processing on the selected two or more band images based on the enhancement amount set for the region where the observation target in the subject is distributed in the feature space formed with the wavelength bands or spatial frequency bands of the two or more band images selected among the plurality of band images generated by the band decomposition processing section 111 set as axes.

(3) Color Conversion Processing

After the enhancement processing has been performed on the selected band images, the color conversion processing section 113 performs a color conversion processing on the 3×N band images (including the band image which is a target of the enhancement processing). The color conversion processing in the color conversion processing section 113 is a processing for adjusting color tone here, in which the color tones of the respective band images are adjusted such that the color tones become similar to the whole color tone of the white light observation image displayed under white light in the normal observation mode.

In addition, color adjustment for improving the contrast of an arbitrary object with respect to the background mucosa may be performed.

In addition, the color conversion processing in the color conversion processing section 113 is performed using a color conversion matrix, for example. Note that the color conversion processing may be performed by using a color conversion table.

Figure 9:
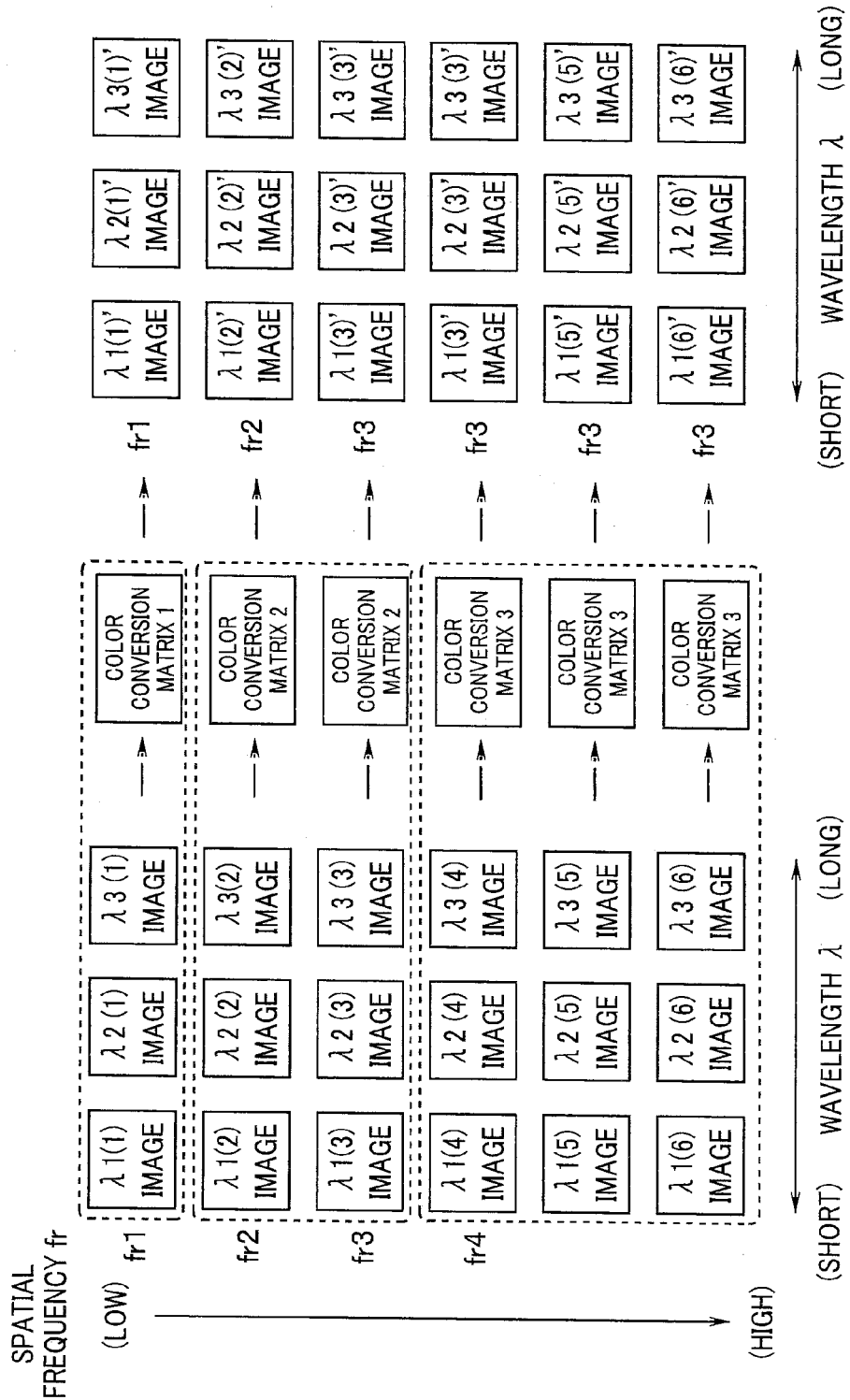
FIG. 9 relates to the embodiment of the present invention and illustrates an example in which a plurality of color conversion matrices are used.

In addition, the color conversion processing section 113 may perform color conversion using a plurality of color conversion matrices. FIG. 9 illustrates an example in which a plurality of color conversion matrices are used.

FIG. 9 illustrates an example in which the respective wavelength images are divided into six frequency bands and a plurality of color conversion matrices are used. For example, a plurality of color conversion matrices may be used such that the color tone of the band image group (band images $\lambda 1$ (1), $\lambda 2$ (1) and $\lambda 3$ (1)) of the spatial frequency fr1 is converted by using a color conversion matrix 1 for low spatial frequency, the color tones of the band image groups (band images $\lambda 1$ (2), $\lambda 2$ (2), . . . (3)) of the spatial frequencies fr2 and fr3 are converted by using a color conversion matrix 2 for intermediate spatial frequency, and the color tones of other band image groups (band images $\lambda 1$ (4), $\lambda 2$ (4), . . . $\lambda 3$ (6)) are converted by using a color conversion matrix 3 for high spatial frequency.

Note that the color conversion matrix is a square matrix of 3×3, for example, and is disclosed in the Japanese Patent No. 3607857, for example.

Therefore, the respective band images are subjected to the color conversion processing after the enhancement processing, or subjected to the color conversion processing without being subjected to the enhancement processing. As a result, 3×N band images subjected to the color conversion processing (and enhancement processing and color conversion processing) (hereinafter such images are referred to as band images after processing) are generated.

In FIG. 4, the $\lambda m$ (k) image subjected to the color conversion processing is shown as the $\lambda m$ (k)' image, for example, that is, the $\lambda 1$ (1) image subjected to the color conversion processing and the like is shown as the $\lambda 1$ (1)' image, and the $\lambda 1$ image subjected to the color conversion is shown as the $\lambda 1$ (2)' image.

Then, the images after processing are integrated for each of the wavelength images, to generate three wavelength images (hereinafter, referred to as integrated wavelength images). The integrated wavelength image (hereinafter referred to as $\lambda 1'$ image) of the $\lambda 1$ image which is an image of the wavelength near 540 nm, the integrated wavelength image (hereinafter referred to as $\lambda 2'$ image) of the $\lambda 2$ image which is an image of the wavelength near 600 nm, and the integrated wavelength image (hereinafter referred to as $\lambda 3'$ image) of the $\lambda 3$ image which is an image of the wavelength near 630 nm are generated.

That is, the image processing section 101 generates, from the 3×N band images after processing, the $\lambda 1'$ image, the $\lambda 2'$ image, and the $\lambda 3'$ image by performing addition, that is, integration on the band images after processing, for each of the wavelengths.

The three images (the $\lambda 1'$ image, the $\lambda 2'$ image and the $\lambda 3'$ image) are supplied to the respective RGB channels of the observation monitor 5 through the selector 102 and the like. As a result, a display image in which the blood vessel or the like at the desired depth is enhanced is displayed on the screen of the observation monitor 5.

Figure 10:
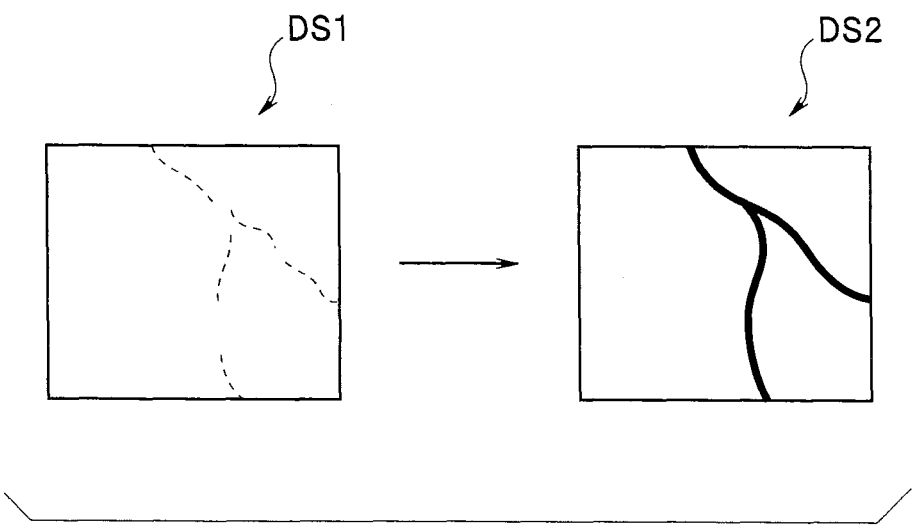
FIG. 10 relates to the embodiment of the present invention and illustrates that a blood vessel at a desired depth is enhanced.

FIG. 10 illustrates that the blood vessel at the desired depth is enhanced. As shown in FIG. 10, the blood vessel in the deep part under the living tissue surface has been poorly displayed in conventional systems as illustrated in the image DS1. In contrast, according to the above-described endoscope system, the blood vessel is enhanced and clearly displayed as illustrated in the image performed.

Note that, in the above-described example, the color conversion processing is perfotined after the enhancement processing was performed on the selected band images. However, after the color conversion processing was performed on all of the band images, the enhancement processing may be performed on the selected band images, to generate band images after processing. Accordingly, the color conversion processing section 113 configures color conversion processing means which performs color conversion processing for adjusting color tone on a plurality of band images before the enhancement processing is performed, or on a plurality of band images including two or more selected band images on which enhancement has been performed by the enhancement processing means.

As a result, it is possible to provide an image processing apparatus and an endoscope system capable of creating, in an enhanced manner, an image of the blood vessel or the like, an image of which is desired to be created and which is located at a desired depth under the living tissue surface, by performing the above-described image processing.

Description was made above on the example in which N band images are generated from the three wavelength images to display one object in an enhanced manner, but it is also possible to set feature spaces and regions as described below, to thereby select objects at various desired depths and display the objects in an enhanced manner.

FIG. 11 illustrates a processing for generating images in a plurality of frequency bands from a plurality of wavelength images and performing the enhancement processing and the like on targets at a plurality of desired depths in the generated images of the plurality of frequency bands.

As shown in FIG. 11, the band decomposition processing section 111 divides the $\lambda 1$ image into images in N (N is a positive integer equal to or larger than 1) spatial frequency bands (hereinafter such images are referred to as band images) by a spatial frequency analysis, or a spatial frequency division, for example. Similarly, the band decomposition processing section 111 divides the $\lambda 2$ image to $\lambda M$ image (M is a positive integer equal to or larger than 2) respectively into N band images. That is, the band decomposition processing section 111 generates N band images for each of the images in M wavelengths.

It is assumed that there are three targets at depths desired to be displayed in an enhanced manner among M×N band images. For example, it is assumed that the blood vessel in the deep part under the surface of mucosa, a pit pattern in the mucosal superficial layer, and capillary vessels in the mucosal superficial layer are desired to be displayed in an enhanced manner.

The blood vessel in the deep part can be displayed in the enhanced manner by performing a processing for multiplying a predetermined enhancement coefficient to the band images $\lambda 2$ (2) to $\lambda M$ (2) as the image group TG1 shown by a one-dot chain line, the pit pattern in the mucosal superficial layer can be displayed in the enhanced manner by performing a processing for multiplying a predetermined enhancement coefficient to the band images $\lambda 3$ (N) to $\lambda M$ (N) as the image group TG2 shown by a one-dot chain line, and the capillary vessel in the mucosal superficial layer can be displayed in the enhanced manner by performing a processing for multiplying a predetermined enhancement coefficient to the band images $\lambda 1$ (N) and $\lambda 2$ (N2) as the image group TG3 shown by a one-dot chain line.

The user sets feature spaces and the regions in the respective feature spaces with respect to the plurality of band images for each of the targets, and further creates enhancement coefficient tables for the respective regions as described above. For example, the user sets a feature space for displaying the blood vessel in the deep part in the enhanced manner as a multidimensional space with (M−1) axes which correspond to the band images $\lambda 2$ (2) to $\lambda M$ (2) shown as the image group TG1, and sets a region of the blood vessel in the deep part in the multidimensional space. Then, the user creates an enhancement coefficient table TBL1 for the region.

Similarly, the user sets a feature space for displaying the pit pattern in the mucosal superficial layer in the enhanced manner as a multidimensional space with (M−2) axes which correspond to the band images $\lambda 3$ (N) to $\lambda M$ (N) shown as the image group TG2, and sets a region of the pit pattern in the mucosal superficial layer in the multidimensional space. Then, the user creates an enhancement coefficient table TBL2 for the region.

Similarly, the user sets a feature space for displaying the capillary vessel in the mucosal superficial layer in the enhanced manner as a two-dimensional space with two axes which correspond to the band images $\lambda 1$ (N) and $\lambda 2$ (N) shown as the image group TG3, and sets a region of the capillary vessel in the mucosal superficial layer in the two-dimensional space. Then, the user creates an enhancement coefficient table TBL3 for the region.

As described above, the user sets the feature spaces and the band images for the desired targets in advance and creates corresponding enhancement coefficient tables in advance. Then, the three enhancement coefficient tables are stored in the memory in the image processing section 101. Note that the tables TBL1 to TBL 3 may be integrated as one table.

When the user selects a target desired to be displayed in the enhanced manner and instructs an enhanced display, a selection signal SS including a signal for selecting the enhancement coefficient table corresponding to the target desired to be displayed in the enhanced manner is supplied from the control circuit 200 to the image processing section 101, and the processings as described above are perfolined in the image processing section 101, thereby allowing the target desired to be enhanced to be displayed on the screen of the observation monitor 5 in the enhanced manner.

For example, the enhanced display of the blood vessel in the deep part is instructed, the $\lambda 1$ to $\lambda M$ images are respectively divided into N band images in the band decomposition processing section 111. The enhancement processing section 112 refers to the enhancement coefficient table TBL1, and performs the enhancement processing on the band images $\lambda 2$ (2) to $\lambda M$ (2) shown as the image group TG1 selected in response to the instruction of the enhanced display of the blood vessel in the deep part. The color conversion processing section 113 performs the color conversion processing for adjusting color tone on the N×M band images including the band images $\lambda 2$ (2) to $\lambda M$ (2) subjected to the enhancement processing, and outputs the $\lambda 1'$ image, the $\lambda 2'$ image, ..., the $\lambda M'$ image which are obtained by performing integration for each of the wavelengths.

In addition, when the enhanced display of the pit pattern in the mucosal superficial layer is instructed, the $\lambda 1$ to $\lambda M$ images are respectively divided into N band images in the band decomposition processing section 111. The enhancement processing section 112 refers to the enhancement coefficient table TBL2, and performs the enhancement processing on the band images $\lambda 3$ (N) to $\lambda M$ (N) shown as the image group TG2 selected in response to the instruction of the enhanced display of the pit pattern in the mucosal superficial layer. The color conversion processing section 113 performs the color conversion processing for adjusting color tone on the N×M band images including the band images $\lambda 3$ (N) to $\lambda M$ (N) subjected to the enhancement processing, and outputs the $\lambda 1'$ image, the $\lambda 2'$ image, ..., $\lambda M'$ image which are obtained by performing integration for each of the wavelengths.

Furthermore, when the enhanced display of the capillary vessel in the mucosal superficial layer is instructed, the $\lambda 1$ to $\lambda M$ images are respectively divided into N band images in the band decomposition processing section 111. The enhancement processing section 112 refers to the enhancement coefficient table TBL3, and performs the enhancement processing on the band images $\lambda 1$ (N) and $\lambda 2$ (N) shown as the image group TG3 selected in response to the instruction of the enhanced display of the capillary vessel in the mucosal superficial layer. The color conversion processing section 113 performs the color conversion processing for adjusting color tone on the N×M band images including the band images $\lambda 1$ (N) and $\lambda 2$ (N) subjected to the enhancement processing, and outputs the $\lambda 1'$ image, the $\lambda 2'$ image, ..., the $\lambda M'$ image which are obtained by performing integration for each of the wavelengths. Note that, when the user desires to enhance all of the blood vessels in the deep part, the pit pattern, and the superficial blood vessel, all the tables TBL1 to TBL3 can be used.

As described above, each of the plurality of wavelength images is decomposed into a plurality of band images, the feature spaces and the regions of the targets are set according to the desired targets, and enhancement coefficients are set for the respective regions. Then, a desired target is specified or selected, thereby capable of enhancing and displaying only the specified or selected target on the observation monitor 5.

The targets under the surface of the living tissue, which are desired to create the images thereof, include a blood vessel in the vicinity of a lesion part located near mucosal superficial layer, a relative thick blood vessel located in a deep part of the mucosa, a submucosal tumor, and the like, and it is possible to create images of such targets located at various depths under the surface of the living tissue, i.e., the blood vessels, a lesion part, or the like at various depths in a more enhanced manner than the blood vessels or the like located at depths other than the above-described depths, and further possible to improve the contrast of a gland opening by observation in which a magnification endoscope is used in combination. As a result, the operation time by the surgeon can be reduced.

Next, modified examples of the present embodiment will be described.

Modified Example 1

In the above-described embodiment, the light source device configured to emit a plurality of narrow band lights is used in order to obtain the reflected lights of the plurality of narrow-band lights. However, white light is irradiated to a subject and a plurality of wavelength images may be obtained from the reflected light of the white light by a spectral estimation processing. For example, in the example shown in FIG. 4, the λ1 image, the λ2 image and the λ3 image may be generated by the spectral estimation processing.

Modified Example 2

In the above-described embodiment, the light source device emits a plurality of narrow-band lights in sequence. However, the light source device may be configured to emit a predetermined plurality of narrow-band lights by allowing the light from the light source lamp of white light to pass through a predetermined interference filter, thereby simultaneously illuminating the plurality of narrow-band lights to the subject and allowing the reflected lights from the subject to pass through a color filter provided on a light-receiving surface of the image pickup device, to simultaneously pickup the images of the reflected lights and obtain a plurality of wavelength images in the output of the image pickup device.

Modified Example 3

In the above-described embodiment, as shown in FIG. 5, the region R and the reference vector RV are set in the feature space with three axes, and then the enhancement coefficients are set in the feature space. However, the three-dimensional feature space may be projected on a two-dimensional feature space, for example, and a region and a reference vector may be set in the two-dimensional feature space.

Figure 12:
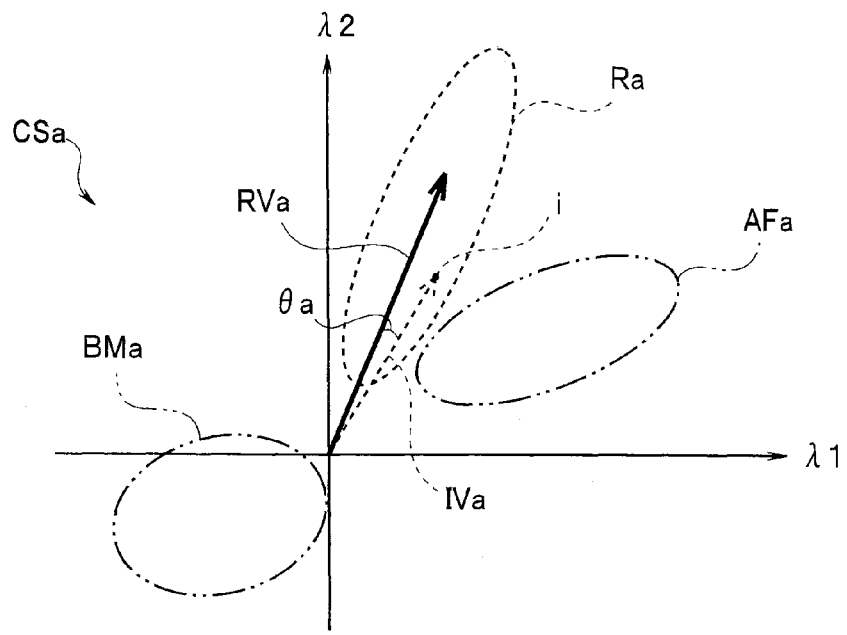
FIG. 12 relates to a modified example of the embodiment of the present invention and illustrates a case where two feature spaces are formed by projecting the three axes in FIG. 5 on two axes.
Figure 13:
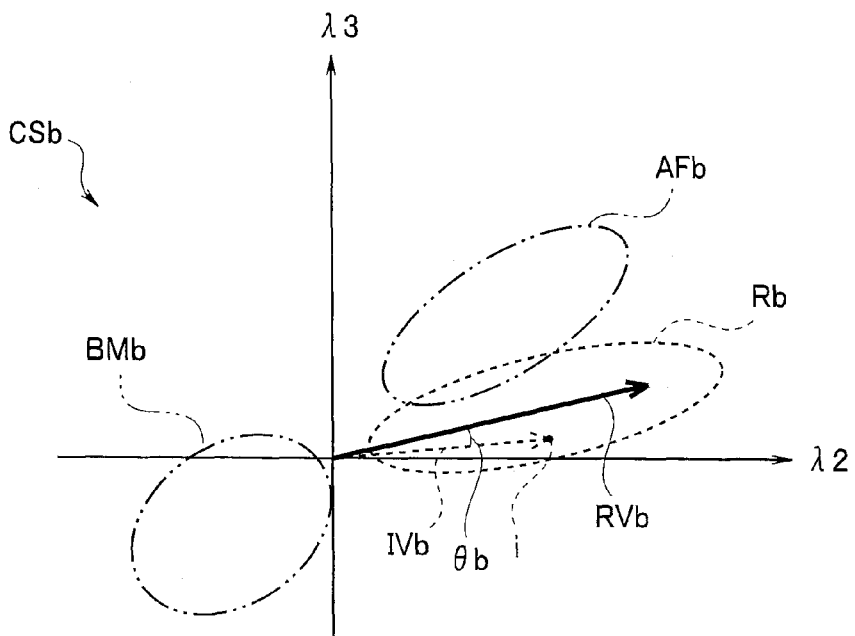
FIG. 13 relates to a modified example 3 of the embodiment of the present invention and illustrates a case where two feature spaces are formed by projecting the three axes in FIG. 5 on two axes.

FIG. 12 and FIG. 13 illustrate a case where two feature spaces are formed by projecting the three axes in FIG. 5 on two axes. FIG. 12 illustrates a case where the region R and the reference vector RV are set in the feature space with the axes of the wavelengths λ1 and λ2. FIG. 13 illustrates a case where the region R and the reference vector RV are set in a feature space with axes of the wavelengths λ2 and λ3.

The three-dimensional feature space is projected on the two feature spaces to be divided into two feature spaces, and reference vectors are set in the respective divided two feature spaces. When enhancement coefficients are set for the set reference vectors and it is supposed that an angle formed between a vector IVa of an arbitrary point i in the feature space CSa and a reference vector RVa is θa, and an angle formed between a vector IVb for the same point i in the feature space CSb and a reference vector RVb is θb, the enhancement coefficient ai may be set using the following Equation (2).

$$\alpha i = (((\pi/2) - \theta a)((\pi/2) - \theta b))^r \quad \text{Equation 2}$$

Modified Example 4

In the above-described embodiment, the region R is set in a space with axes of a plurality of wavelengths or frequency bands, and the enhancement amount with respect to the reference vector RV is set. However, the space is projected on another space and an enhancement coefficient may be set in the projected space.

Figure 14:
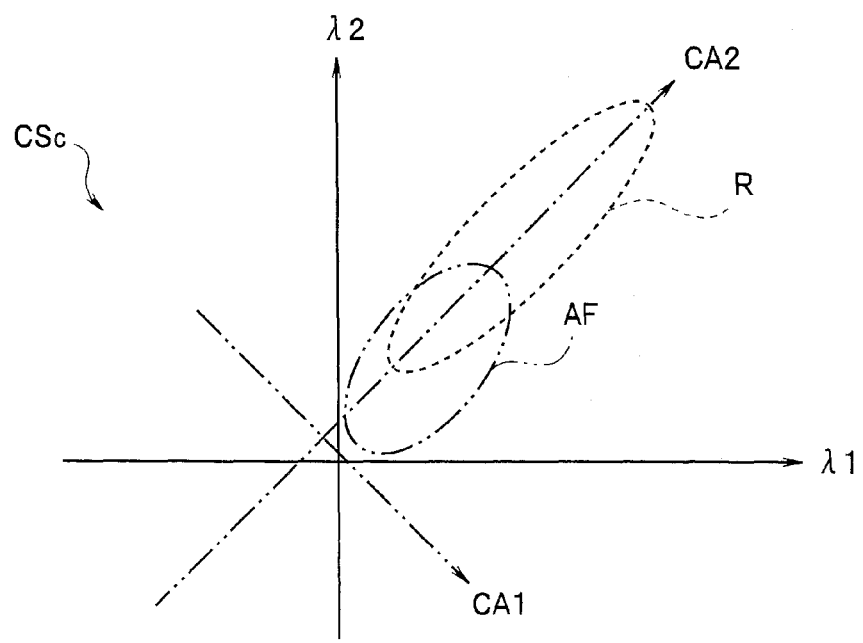
FIG. 14 relates to a modified example 4 of the embodiment of the present invention and illustrates a region R and an artifact AF in a two-dimensional feature space CSc having two axes of certain wavelengths $\lambda 1$ and $\lambda 2$.
Figure 15:
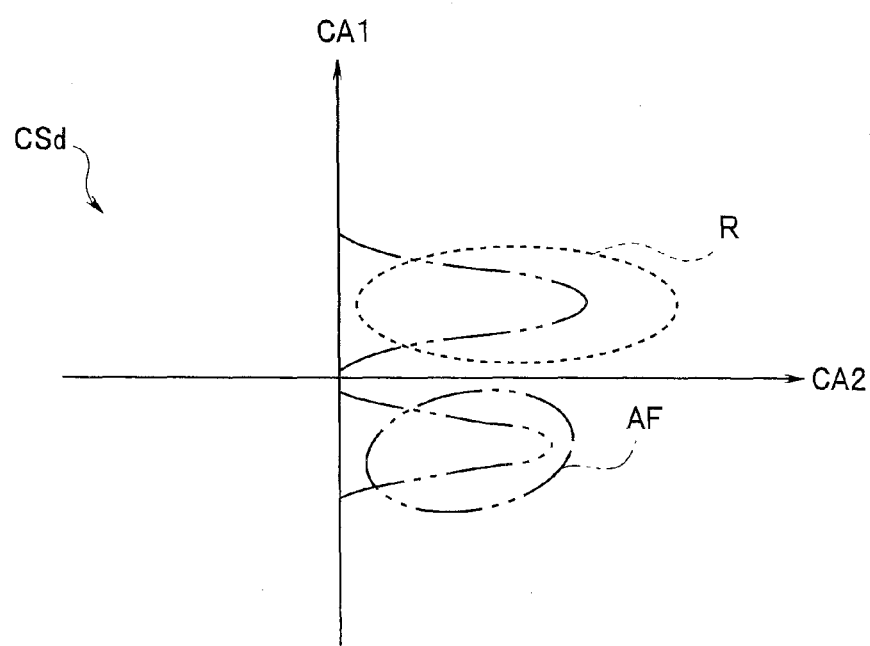
FIG. 15 relates to the modified example 4 of the embodiment of the present invention and illustrates the region R and the artifact AF at the time that the feature space CSc in FIG. 14 is projected on another feature space CSd.

FIG. 14 illustrates the region R and the artifact AF in a two-dimensional feature space CSc with two axes of certain wavelengths λ1 and λ2. FIG. 15 illustrates the region R and the artifact AF when the feature space CSc in FIG. 14 is projected on another feature space CSd.

In FIG. 14, it is hard to set an enhancement coefficient since the region R and the artifact AF overlap each other. On the other hand, as shown in FIG. 15, in the feature space CSd obtained by projecting the feature space CSc in the space formed with the axis CA1 perpendicular to the reference vector RV and the axis CA2 parallel to the reference vector RV, the region R of an observation target and the artifact AF are distributed in different regions, which makes it easier to set the enhancement coefficient.

Therefore, the enhancement amount may be set in a feature space obtained by projecting a feature space in another feature space different from the space with wavelength axes or the space with band frequency axes.

As described above, according to the above-described embodiment and the respective modified examples, it is possible to provide the image processing apparatus and the endoscope system capable of creating, in an enhanced manner, the images of a blood vessel and the like, images of which are desired to be created and which are located at desired depths under the surface of the living tissue. As a result, it is possible to reduce the treatment time.

Furthermore, it is possible to increase the detection rate of a submucosal tumor which is difficult to be visually recognized under white light observation.

The present invention is not limited to the above-described embodiment, but various changes and modifications are possible without departing from the gist of the present invention.

What is claimed is:

1. An image processing apparatus comprising:
   an image input section that receives a medical image picked up in a subject;
   a band decomposition processing section that performs decomposition processing respectively on images in a plurality of wavelength bands in the medical image, to decompose the respective images into images in a plurality of spatial frequency bands and generate a plurality of band images;
   an enhancement amount setting section that selects two or more band images among the plurality of band images generated by the band decomposition processing section according to an observation target which exists in a depth direction of a living mucosa in the subject, and sets an enhancement amount for a region where the observation target in the subject is distributed in a feature space, the feature space being a space formed so as to have, as axes, wavelength bands or spatial frequency bands of the selected two or more band images, or being another space in which the space is projected;
   an enhancement processing section that performs enhancement processing on the selected two or more band images, based on the enhancement amount set by the enhancement amount setting section;
   a color conversion processing section that performs color conversion processing for adjusting color tone on the plurality of band images before the enhancement processing is performed thereon, or the plurality of band images including the selected two or more band images having been enhanced by the enhancement processing section; and
   an image generation section that integrates the plurality of band images subjected to the color conversion processing by the color conversion processing section, for each wavelength image, to generate an image.

2. The image processing apparatus according to claim 1, wherein the observation target is a blood vessel in a deep part under a surface of mucosa, a pit pattern in a mucosal superficial layer, or a capillary vessel in a mucosal superficial layer.

3. The image processing apparatus according to claim 1, wherein the enhancement amount setting section sets the enhancement amount by storing the enhancement amount in a table as table data.

4. The image processing apparatus according to claim 3, wherein the table data is an enhancement coefficient for an pixel value of each pixel in the respective band images.

5. The image processing apparatus according to claim 3, wherein the enhancement amount setting section sets a plurality of regions where the observation target is distributed, and the table is provided for each of the set regions.

6. The image processing apparatus according to claim 5, wherein the table provided for each of the regions is selectable.

7. The image processing apparatus according to claim 1, wherein the medical image is an image generated by spectral estimation processing.

8. The image processing apparatus according to claim 2, wherein the enhancement amount setting section sets, with respect to a region where a blood vessel which exists in a depth direction of a living mucosa in the subject is distributed in the feature space, one, or two or more reference vectors and a point vector from an origin in the feature space to a predetermined pixel value data in the region where the blood vessel is distributed, and sets the enhancement amount based on an angle displacement amount calculated from an angle formed between the reference vector and the point vector.

9. The image processing apparatus according to claim 8, wherein the enhancement processing section performs the enhancement processing only on pixels located on a side of the one, or two or more reference vectors with a plane perpendicular to the reference vectors in the feature space and including the origin in the feature space, as a reference.

10. The image processing apparatus according to claim 1, wherein the enhancement amount setting section sets the enhancement amount so as not to enhance blood vessels in a living body, a background mucosa, and other targets, in the feature space.

11. The image processing apparatus according to claim 1, wherein the decomposition processing by the band decomposition processing section is spatial frequency filtering processing.

12. An endoscope system comprising:
an illuminating section that irradiates light having a plurality of wavelength bands to a subject;
an image pickup section that picks up an image of returned light of the light irradiated to the subject by the illuminating section;
a band decomposition processing section that performs decomposition processing for decomposing into a plurality of spatial frequency bands respectively on images in a plurality of wavelength bands generated from signals of the image picked up by the image pickup section and generates a plurality of band images;
an enhancement amount setting section that selects two or more band images among the plurality of band images generated by the band decomposition processing section, and sets an enhancement amount for a region where a blood vessel which exists in a depth direction of a living mucosa in the subject is distributed in a feature space, the feature space being a space formed so as to have, as axes, wavelength bands or spatial frequency bands of the selected two or more band images, or being another space in which the space is projected;
an enhancement processing section that performs enhancement processing on the selected two or more band images, based on the enhancement amount set by the enhancement amount setting section;
a color conversion processing section that performs color conversion processing for adjusting color tone on the plurality of band images before the enhancement processing is performed thereon, or the plurality of band images including the selected two or more band images having been enhanced by the enhancement processing section;
an image generation section that integrates the plurality of band images subjected to the color conversion processing by the color conversion processing section, for each wavelength image, to generate an image;
a display signal output section that outputs an integrated image outputted from the image generation section as a display signal; and
a display section that performs display based on the display signal outputted from the display signal output section.

13. The endoscope system according to claim 12, wherein the illuminating section irradiates the light having the plurality of wavelengths bands in time series or simultaneously.

14. The endoscope system according to claim 12, wherein the band decomposition processing section performs the decomposition processing on the images in the plurality of wavelength bands which are obtained by spectral estimation processing from signals of the picked up image.

* * * * *